US011447780B2

United States Patent

(12) United States Patent
Zamyatnin et al.
(10) Patent No.: US 11,447,780 B2
(45) Date of Patent: Sep. 20, 2022

(54) PREPARATION OF WHEAT CYSTEINE PROTEASE TRITICAIN-ALPHA PRODUCED IN SOLUBLE FORM AND METHOD OF PRODUCING SAME

(71) Applicant: FEDERAL STATE AUTONOMOUS EDUCATIONAL INSTITUTION OF HIGHER EDUCATION I.M. SECHENOV FIRST MOSCOW STATE MEDICAL UNIVERSITY OF THE MINISTRY OF HEALTHCARE OF THE RUSSIAN FEDERATION (SECHENOVSKIY UNIVERSITY), Moscow (RU)

(72) Inventors: Andrey Aleksandrovich Zamyatnin, Moscow (RU); Evgeniy Yurievich Zerniy, Moscow (RU); Neonila Vasilievna Gorokhovets, Moscow (RU); Natalia Viktorovna Kuznetcova, Moscow (RU); Vladimir Alekseevich Makarov, Podolsk (RU); Liudmila Vladimirovna Savvateeva, Moscow (RU); Vadim Vladimirovich Tarasov, Moscow (RU)

(73) Assignee: FEDERAL STATE AUTONOMOUS EDUCATIONAL INSTITUTION OF HIGHER EDUCATION I.M. SECHENOV FIRST MOSCOW STATE MEDICAL UNIVERSITY OF THE MINISTRY OF HEALTHCARE OF THE RUSSIAN FEDERATION (SECHENOVSKIY UNIVERSITY), Moscow (RU)

( * ) Notice: Subject to any disclaimer, the term of this patent is extended or adjusted under 35 U.S.C. 154(b) by 94 days.

(21) Appl. No.: 16/626,206

(22) PCT Filed: Jun. 28, 2018

(86) PCT No.: PCT/RU2018/050071

§ 371 (c)(1),
(2) Date: Dec. 23, 2019

(87) PCT Pub. No.: WO2019/004878

PCT Pub. Date: Jan. 3, 2019

(65) Prior Publication Data

US 2022/0162619 A1 May 26, 2022

(30) Foreign Application Priority Data

Jun. 28, 2017 (RU) .......................... RU2017122806

(51) Int. Cl.
*C12N 15/70* (2006.01)
*C12N 9/52* (2006.01)
*C12N 15/11* (2006.01)

(52) U.S. Cl.
CPC .............. *C12N 15/70* (2013.01); *C12N 9/52* (2013.01); *C12N 15/11* (2013.01); *C12Y 304/22002* (2013.01)

(58) Field of Classification Search
None
See application file for complete search history.

(56) References Cited

FOREIGN PATENT DOCUMENTS

RU 2603054 C2 11/2016

OTHER PUBLICATIONS

Vora H. et al., "A scaleable manufacturing process for pro-EP-B2, a cysteine protease from barley indicated for celiac sprue.", Biotechnol Bioeng. Sep. 1, 2007 ;98(1):177-85, https://doi.org/10.1002/bit.21423, abstract, retrieved on Dec. 31, 2019.

Savvateeva, "Glutenase and collagenase activities of wheat cysteine protease Triticain-α: feasibility for enzymatic therapy assays", Int J Biochem Cell Biol. May 2015;62:115-24. doi: 10.1016/j.biocel.2015.03.001. Epub Mar. 10, 2015.

International Search Report dated Nov. 29, 2018 in respect of the International Patent Application PCT/RU2018/050071.

*Primary Examiner* — Suzanne M Noakes
*Assistant Examiner* — Jae W Lee
(74) *Attorney, Agent, or Firm* — BCF LLP

(57) ABSTRACT

The invention relates to the field of molecular biology, preparative biochemistry, biotechnology, and biopharmacology, namely to the creation of recombinant proteins of the family of wheat (*Triticum aestivum*) cysteine proteases in soluble form, and preparations of the protein triticain-alpha consisting of a fragment of wheat triticain-alpha and methods for the production thereof. The invention can be used for research purposes to study the functioning of papain-like cysteine proteases, as well as in medicine for developing therapeutic enzyme preparations, and is a method of producing, in soluble form, recombinant functionally active variants of wheat (*Triticum aestivum*) cysteine proteases, including the engineering of plasmid DNA for cloning in expression systems of *E. coli* and *P. Pastoris*. By transforming cells of *E. coli* of the strain Rossetta gami B (DE3) and cells of *P. pastoris* of the strain GS115 by plasmid DNA pET15-6HIS-tritcain-α-GM, pET15-triticain-α-GM-6HIS, and pPIC9-tritcain-α-GM respectively, truncated producing strains of wheat triticain-alpha are obtained, with subsequent culturing of host cells, separation of expressing protein, and purification by chromatographic methods. The invention allows variants of a biologically active fragment of wheat protease to be produced in soluble form in bacteria and yeast expression systems and allows the preparation triticain-alpha to be produced with a high, stable output, purity level and functional activity.

1 Claim, 3 Drawing Sheets

Specification includes a Sequence Listing.

PREPARATION OF WHEAT CYSTEINE PROTEASE TRITICAIN-ALPHA PRODUCED IN SOLUBLE FORM AND METHOD OF PRODUCING SAME

ELECTRONIC FILE—SEQUENCE LISTING

This application hereby incorporates by reference the material of the electronic Sequence Listing filed concurrently herewith. The material in the electronic Sequence Listing is submitted as a text (.txt) file entitled "104525-002-SEQ-listing.txt" created on May 4, 2022, which has a file size of 8,755 bytes, and is herein incorporated by reference in its entirety.

TECHNICAL FIELD

The invention relates to the field of molecular biology, preparative biochemistry, biotechnology, biopharmacology, namely to the creation of methods for producing recombinant proteins of the wheat (*Triticum aestivum*) cysteine protease family in soluble form and preparations of the triticain-alpha, containing fragment of wheat triticain-alpha. The invention can be used for research purposes to study the functioning of papain-like cysteine protease, as well as in medicine for the development of enzyme therapeutic preparations.

STATE OF THE ART

Triticains (triticain-α, triticain-β, and triticain-γ) are highly conserved papain-like wheat cysteine endoprotease, consisting of a signal (leader) peptide which is deleted when the pro-peptide domain is activated, a granulin-like domain [GenBank AB267407], and a catalytic domain with the catalytic Cys-His-Asn triad [T. Kiyosaki, T. Asakura, I. Matsumoto, et al. J Plant Physiol, 2009, 1, 166(1), 101-6]. Cysteine protease are common in plants and expressed in their various organs [K. Muntz, M. A. Belozersky, Y. E. Dunaevsky, et al. J Exp Bot, 2001, 52, 1741-52; J. Q. Ling, T. Kojima, M. Shiraiwa, et al. Biochim Biophys Acta, 2003, 1627, 129-39]. These enzymes are assumed to be involved in the stage-specific cleavage and post-translational modifications of storage proteins [A. Capocchi, M. Cinollo, L. Galleschi, et al. J Agric Food Chem, 2000, 48, 6271-79; T. Okamoto, T. Shimada, I. Hara-Nishimura, et al. Plant Physiol, 2003, 132, 1892-1900]. Among all papain-like plant cysteine proteases, two enzymes from rice and barley, namely, oryzains (oryzain-α, oryzain-β, and oryzain-γ) and EPB endopeptidases (barley cysteine protease B-1 and B-2) are most widely studied [A. Mikkonen, I. Porali, M. Cercos, et al. Plant Mol Biol, 1996, 31(2), 239-54; H. Kondo, K. Abe, I. Nishimura, et al. J Biol Chem, 1990, 15, 265(26), 15832-37], but wheat proteases have begun to be studied relatively recently [T. Kiyosaki, T. Asakura, I. Matsumoto, et al. J Plant Physiol, 2009, 1, 166(1), 101-6; T. Kiyosaki, I. Matsumoto, T. Asakura, et al. FEBS J, 2007,274, 1908-17].

The main advantage of papain-like cysteine protease from plant seeds at the moment is their endopeptidase activity, in particular, glutenase activity, i.e. the ability to effectively hydrolyze the peptides of gluten (a storage protein of wheat, consisting of mixture of monomeric gliadins and polymeric glutenins) or those of related storage proteins of rye and barley. Such property of plant enzymes allows considering them promising objects in the design of drugs to treat celiac disease. Celiac disease (gluten enteropathy) is a human complex inflammatory disease, which develops under an appropriate genetic predisposition in response to peptides enriched in proline and glutamine residues, which are the products of partial gluten proteolysis in the human digestive tract [N. McGough, J. H. Cummings. Proc Nutr Soc, 2005, 64(4), 434-50; J. S. Leeds, A. D. Hopper, D. S. Sanders. Br Med Bull, 2008, 88(1), 157-70]. The prevalence of celiac disease in the adult population of most countries in the world is estimated as 1:100-1:250 or 0.5-1% of the total population [WGO-OMGE: Practice guidelines. World Gastroenterology News, 10 (2, 2), 2005, 1-8]. Strict lifetime adherence to a gluten-free diet is the only proven effective treatment for celiac disease, which can prevent the development of complications and eliminate the disease's clinical symptoms [S. Rashtak, J. A. Murray. Aliment Pharmacol Ther, 2012, 35(7), 768-81]. However, the main drawback of the gluten-free diet is the difficulty of following it due to its restrictive nature, because of the high cost and the complexity of one's selection of gluten-free foods.

In this regard, the research and design of methods to produce highly specific protease which are stable and active in the presence of endogenous enzymes in the human gastrointestinal tract (i.e., in the localization of the intended action of a drug based thereon) is of great importance for therapeutic purposes [L. V. Savvateeva, A. A. Zamyatnin. Curr Pharm Des, 2016, 22(16), 2439-49].

The method for producing the proenzyme form of barley cysteine protease EP-B2 is known from the literature [H. Vora, J. McIntire, P. Kumar, et al. Biotechnol Bioeng, 2007, 1, 98(1), 177-85, application WO2008115428 A2, Sep. 25, 2008].

In our invention, the protease of wheat *Triticum aestivum* (triticain-alpha) was chosen, because the wheat plays a significant role as a food source in Russia, which means it is most suitable for the development of domestic therapeutic drugs to treat celiac disease.

The full-size triticain-alpha molecule consists of 461 amino acid residues with a molecular weight of 50.4 kDa. For the first time, this enzyme was cloned and expressed in the germ and aleurone layer of wheat to elucidate its role in the process of seed maturation [T. Kiyosaki, T. Asakura, I. Matsumoto, et al. J Plant Physiol, 2009, 1, 166(1), 101-6]. However, triticain-alpha itself was not isolated.

The biosynthesis of recombinant triticain-alpha to study its proteolytic functions was carried out by us earlier [L. V. Savvateeva, N. V. Gorokhovets, V. A. Makarov, et al. Int J Biochem Cell Biol, 2015, 62, 115-24, Patent RU 2603054 C2, Nov. 20, 2016]. In the described method, recombinant triticain-alpha (a fragment of the full-sized protein) was synthesized in bacterial cells in an insoluble form, which required the inclusion of an additional (hardly validated) stage of refolding in the process of isolating the target protein. Moreover, the resulting preparations had lower activity than the preparations obtained in this application, and also had a lower yield upon isolation and lower purity.

DISCLOSURE OF THE INVENTION

The problem to be solved within the framework of this application is to expand the assortment of enzyme preparations with the potential for use as a medicine, as well as to develop an effective method for producing a highly purified and highly active protein preparation with subsequent potential use in an industrial environment. There is a need to develop improved economically feasible technologies for the production of such proteins while maintaining the high quality (purity, yield, and activity) of such preparations for research and applied purposes.

The technical result of the present invention is obtaining a highly purified and highly active preparation of a fragment of wheat protease triticain-alpha, consisting of a propeptide domain (prodomain) and a catalytic domain of the full-sized wheat triticain-alpha (i.e. without leader peptide and without granulin-like domain), in soluble form with high yield upon isolation, intended for basic and applied research (in particular, for use as part of enzyme therapeutic agents).

The problem is solved by the biologically active protein preparation with the high specific activity of papain-like cysteine protease, consisting of a fragment (SEQ ID NO:2-4) of the triticain-alpha sequence (SEQ ID NO:1), expressed in soluble form, whose purity is not less than 85%. Moreover, the preparation wherein the triticain-alpha fragment contains a hexahistidine sequence at the N-terminus has the sequence SEQ ID NO:2, the preparation having a hexahistidine sequence at the C-terminus has the sequence SEQ ID NO:3, and the preparation containing no hexahistidine sequence at the C-terminus and N-terminus, has the sequence SEQ ID NO:4.

The problem is also solved by the method for producing a biologically active protein preparation with the specific activity of papain-like cysteine protease, recombinant expression in a bacterial system, which consists in culturing *E. coli* cells of the strain Rosetta gami B (DE3) transformed with the pET15-6HIS-Triticain-α-GM or pET15-Triticain-α-GM-6HIS plasmids containing the DNA sequences encoding proteins with SEQ ID NO:2-3, respectively, in LB medium with ampicillin added at 37° C. under aerobic conditions for 12-14 h; The nutrient medium is inoculated with the sowing material, the culture is grown until the optical density $A_{600}$ is 0.6-0.8, is induced with 1 mM isopropylthio-β-D-galactoside and grown for another 20 h at 18° C. with the accumulation of the protein's soluble form with SEQ ID NO:2-3; Further, the expression cultures precipitated by centrifugation are resuspended in 0.02 M phosphate buffer, pH 8.0, containing 0.5 M NaCl and 0.01 M imidazole (buffer A), and homogenized on an ultrasonic disintegrator for 1 min at 4° C.; The corresponding supernatant obtained after centrifugation of lysates is applied onto a column with nickel-activated iminodiacetate-sepharose equilibrated in buffer A, the sorbent is washed successively with the equilibrated buffer A, then the protein is eluted with buffer A containing 0.3 M imidazole; Then the protein solution is dialyzed against 0.02 M phosphate buffer, pH 8.0 and, after analyzing the concentration and proteolytic activity of the protein with SEQ ID NO:2-3 in the resulting preparation, is aliquoted into glass vials, frozen and lyophilized. In this case, the nucleic acid encoding the protein with SEQ ID NO:2-3 is used, and the vector based on pET15b is used as the expression vector.

The problem is also solved by the method of obtaining a biologically active protein preparation with the high specific activity of papain-like cysteine protease, recombinant expression in a yeast system, which consists in cultivating *P. pastoris* cells of the strain GS115 ($His^-$, $Mut^+/Mut^S$) transformed by the pPIC9-Triticain-α-GM plasmid, containing the DNA sequence encoding the protein with SEQ ID NO:4 in YPD medium at 30° C. in a shaker incubator until the optical density $A_{600}$ reaches 1.5; The cell suspensions are spread in a Petri dish with a minimal histidine-free agarized medium and incubated at 30° C. until colonies appear; Then one colony of the obtained *Pichia pastoris* GS115/pPIC9-Triticain-α-GM transformants containing one or two copies of the truncated triticain-alpha gene fragment is used to inoculate the nutrition medium BMGY and the cell mass is increased at 30° C. in the shaker incubator to an optical density of 5 o.u. ($Mut^+$) or 25 o. u. ($Mut^S$), precipitated by centrifugation and the precipitate is resuspended in BMMY medium, followed by incubation for 96 h at 30° C. and 300 rpm, adding methanol as an expression inducer every 24 h to a final concentration of 0.7%; Then the cells are precipitated, supernatants are selected; Then the culture supernatant of *Pichia pastoris* GS115/pPIC9-Triticain-α-GM is filtered (0.45 μm) and dialyzed against a 0.02 M sodium phosphate solution, pH 8.0 at 4° C. for 24 h, the dialysate is concentrated and applied to a column with a Sephacryl S-200HR sorbent, equilibrated in 0.02 M phosphate buffer, pH 8.0, containing 130 mM NaCl; Then 6 ml of each protein fraction is collected and analyzed for the presence of the protein (SEQ ID NO:4) by electrophoretic analysis and the concentration and proteolytic activity are estimated, then the biologically active protein preparation is aliquoted into glass vials, frozen and lyophilized. In this case, to implement the method, the nucleic acid encoding the protein with the sequence SEQ ID NO:4 and the pPIC9-based expression vector are used in the method for producing the biologically active protein preparation.

IMPLEMENTATION OF THE INVENTION

Figure 1:
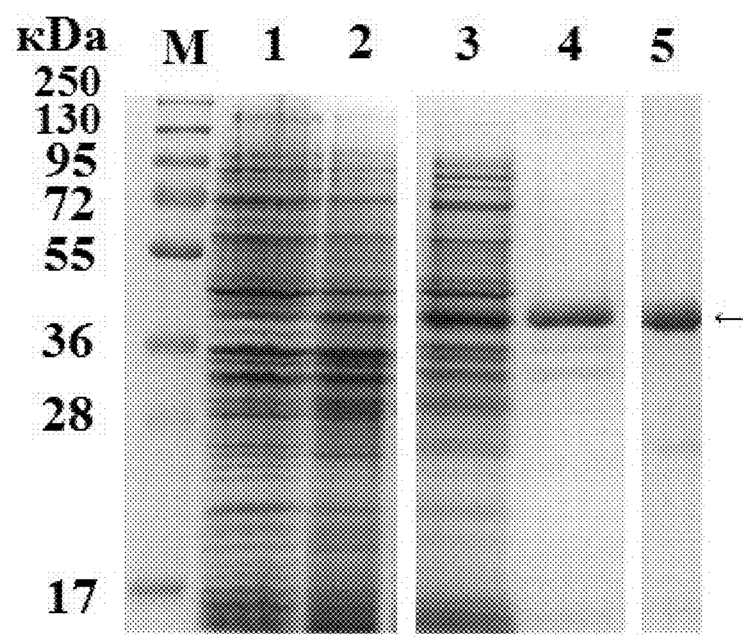
FIG. 1 shows the electrophoregram of the following substances in a 12% polyacrylamide gel in the presence of SDS: cell lysates of the producer *E. coli* strain Rosetta gami B (DE3)/pET15-6HIS-Triticain-α-GM before induction (lane 1), cell lysates of the producer *E. coli* strain Rosetta gami B (DE3)/pET15-6HIS-Triticain-α-GM after induction with isopropylthio-β-D-galactoside (lane 2); the soluble cell fraction (lane 3), the insoluble cell fraction (lane 4); the recombinant truncated triticain-alpha (SEQ ID NO:2, 6HIS-Triticain-α-GM, lane 5) after chromatographic isolation; M are protein markers of molecular weight (kDa).

In the sequence listing in SEQ ID NO:1, the amino acid and nucleotide sequences of the recombinant full-sized triticain-alpha expressed in *E. coli* are shown (TRIT-α, the sequence from the expression plasmid pET-42a(+) is shown in italics; the restrictase-recognized sites are highlighted in italics and underlined; the leader peptide is underlined; the Cys-His-Asn catalytic triad identifying the protein as a cysteine protease is highlighted in italics and color; the granulin-like domain is highlighted in color; and the restrictase-recognized sites are highlighted by underlining); In SEQ ID NO:2—the amino acid and nucleotide sequences of the recombinant truncated triticain-alpha with an N-terminal polyhistidine sequence expressed in soluble form in *E. coli* (6HIS-Triticain-α-GM; the sequence from the expression plasmid pET-15b is shown in italics; the restrictase-recognized sites are highlighted by underlining; and the Cys-His-Asn catalytic triad determining the protein as a cysteine protease is in italics and color); In SEQ ID NO:3—the amino acid and nucleotide sequences of the recombinant truncated triticain-alpha with a C-terminal polyhistidine sequence expressed in soluble form in *E. coli* (Triticain-α-GM-6HIS; the sequence from the expression plasmid pET-15b is shown in italics; the restrictase-recognized sites are highlighted by underlining; and the Cys-His-Asn catalytic triad determining the protein as a cysteine protease is in italics and color); In SEQ ID NO:4—the amino acid and nucleotide sequences of the recombinant truncated triticain-alpha expressed in *P. pastoris* (y-Triticain-α-GM; the sequence from the expression plasmid pPIC9 is indicated in italics; the α-factor is highlighted in color; the signal of elimination α-factor is marked with an arrow; and the restrictase-recognized sites are underlined);

The present invention is illustrated by several specific examples of implementation, which do not limit its claimed scope, though clearly demonstrate the ability to achieve the desired technical result.

EXAMPLE 1

Cloning of Truncated Fragments of the Triticain-Alpha Gene for Bacterial Expression of Proteins in Soluble Form Based on the known wheat (*Triticum aestivum*) mRNA sequence encoding the full-size triticain-alpha gene (GenBank AB267407), the complementary DNA (cDNA) is synthesized using the reverse transcriptase of the mouse Molony leukemia virus and the primer on the 3'-untranslated mRNA region 5'-gctgctgctgctgctgctgctgctgct-3' (SEQ ID NO: 5). The DNA encoding the translational region of the full-size triticain-alpha gene and flanked by the NdeI and BamHI restriction sites (TRIT-α, SEQ ID NO:1) is amplified using the following direct and reverse primers: 5'-ccccatatgcatcatcatcatcatcatgccatgaggagctccatggccctc-3' (SEQ ID NO: 6) and 5'-gggggatccttacgcgctacttttcttgccg-3' (SEQ ID NO: 7) (the restriction sites NdeI and BamHI are underlined). The amplification product and plasmid DNA pET-42a(+) are treated with restriction enzymes NdeI and BamHI, coupled by the ligase reaction, after which the reaction mixture is transfected into competent *E. coli* cells BL21-CodonPlus (DE3)-RIL. The transformed cells are seeded on LB agar medium containing an antibiotic (kanamycin). Of the PCR-selected clones (using universal primers for pET vectors), the target plasmid DNA (pET_TRIT-α) is isolated. The nucleotide sequence of the inserted fragment is confirmed by Sanger sequencing. The selected clones are expanded to evaluate their productivity, antibiotic resistance and transformation stability.

A new DNA sequence encoding a truncated fragment of the triticain-alpha gene (6HIS-Triticain-α-GM, with no leader peptide and no granulin-like domain, with an N-terminal polyhistidine sequence, SEQ ID NO:2) for expression in a bacterial system, is constructed based on the plasmid DNA pET_TRIT-α as a template and primers: 5'-tatacatatgtcgatcgtgtcgtacgg-3' (SEQ ID NO: 8) (the NdeI restriction site is underlined) and 5'-ttctcgagttagcccgtcttcgtcgg-3' (SEQ ID NO: 9) (the XhoI restriction site is underlined). The amplification product is cloned into the expression plasmid pET-15b (Novagen, Germany) at the NdeI and XhoI restriction sites using *E. coli*, the strain Rosetta gami B (DE3). Colonies are screened by restriction analysis and subsequent sequencing.

In a similar manner, a new DNA sequence encoding a truncated fragment of the triticain-alpha gene (Triticain-α-GM-6HIS), with no leader peptide and no granulin-like domain, with a C-terminal polyhistidine sequence, SEQ ID NO:3) is constructed using the following pair of primers: 5'-ataccatggcgctgccggagaccgtcg-3' (SEQ ID NO: 10) and 5'-attctcgagtcagtggtggtggtggtggtggcccgtcttcgtcgggt-3' (SEQ ID NO: 11) and the restriction sites NcoI and XhoI, respectively (underlined).

EXAMPLE 2

Cloning of a Gene Fragment of Triticain-Alpha for Yeast Protein Expression in Soluble Form A new DNA sequence encoding a truncated fragment of the triticain-alpha gene (y-Triticain-α-GM, SEQ ID NO:4) for expression in a yeast system is constructed on the basis of the plasmid DNA pET_TRIT-α as a template and the following primers: 5'-tgaattctccatcgtgtcgtacggg-3' (SEQ ID NO: 12) (the EcoRI restriction site underlined) and 5'-attgcggccgcttagcccgtcttcgtcgg-3' (SEQ ID NO: 13) (the NotI restriction site underlined). The amplification product is cloned into the *Pichia pastoris* pPIC9 expression vector at the indicated sites, which allows the target protein to be secreted by the signal sequence (α-factor).

EXAMPLE 3

Expression of the Wheat Triticain-Alpha Fragment in Soluble form in *E. coli*

The *E. coli* strain Rosetta gami B (DE3) transformed with the plasmid pET15-6HIS-Triticain-α-GM is grown in LB medium (10 g/L tryptone, 5 g/L yeast extract, 5 g/L NaCl) at 37° C. under aerobic conditions, with ampicillin added (to a final concentration of 50 mg/mL) for 12-14 h (the seeding material), a new portion of the nutrient medium is inoculated in a 1:50 ratio, the culture is grown until the optical density $A_{600}$ is 0.6-0.8, cooled on ice for 15 min and induced with isopropylthio-β-D-galactoside (IPTG) to a final concentration of 1 mM, after which the cells continue to be incubated for 20 h at 18° C. Upon induction with IPTG, the biosynthesis of recombinant 6HIS-Triticain-α-GM (SEQ ID NO:2) proceeds, which accumulates in cells in both soluble form and inclusion bodies (FIG. 1). Cell suspension samples are taken before and after induction in an amount corresponding to 0.1 optical units (o.u.), precipitated by centrifugation, suspended in lysis buffer (0.03 M Tris-HCl, pH 6.8, 10% glycerol, 1% sodium dodecyl sulfate, 3% mercaptoethanol, 0.005% bromophenol blue), heated for 5 min at 95° C., and samples with a volume of 20 μl are analyzed by electrophoresis in a 12% polyacrylamide gel with sodium dodecyl sulfate. The gel is stained with Coomassie R-250 according to standard procedures and scanned to analyze the relative amount of protein in the target protein band (FIG. 1). According to the scan, the content of recombinant 6HIS-Triticain-α-GM is 15-20% of all cellular proteins.

Figure 2:
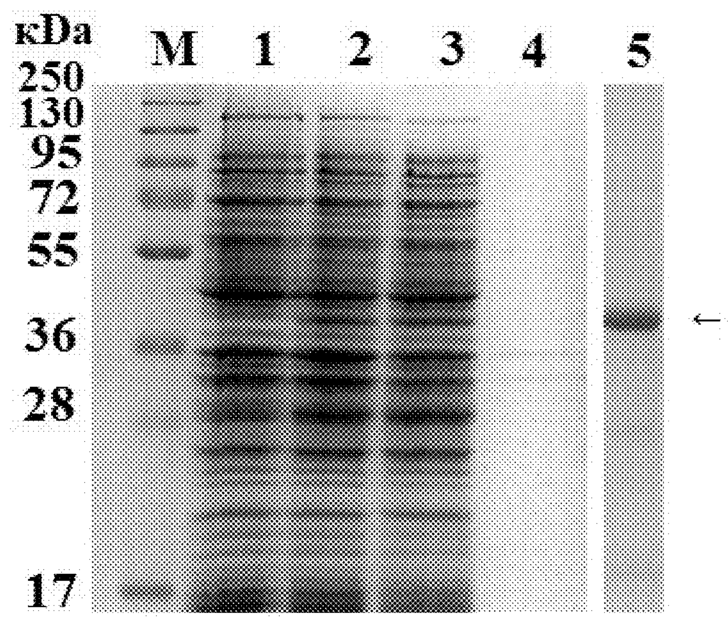
FIG. 2 shows the electrophoregram of the following substances in a 12% polyacrylamide gel in the presence of SDS: cell lysates of the producer *E. coli* strain Rosetta gami B (DE3)/Triticain-α-GM-6HIS before induction (lane 1), cell lysates of the producer *E.coli* strain Rosetta gami B (DE3)/Triticain-α-GM-6HIS after induction with isopropylthio-β-D-galactoside (lane 2); the soluble cell fraction (lane 3), the insoluble cell fraction (lane 4); the recombinant truncated triticain-alpha (SEQ ID NO:3, Triticain-α-GM-6HIS, lane 5) after chromatographic isolation; M are protein markers of molecular weight (kDa).

Similarly, the triticain-alpha fragment of Triticain-α-GM-6HIS (SEQ ID NO:3) is expressed using cells of the Rosetta gami B strain (DE3) transformed with the pET15-Triticain-α-GM-6HIS plasmid. The result of the recombinant protein biosynthesis is analyzed by electrophoresis in a 12% polyacrylamide gel with sodium dodecyl sulfate (FIG. 2). According to gel scanning, the content of recombinant Triticain-α-GM-6HIS is 15-20% of all cellular proteins, and the target protein is synthesized in bacterial cells exclusively in soluble form.

EXAMPLE 4

Production Highly Purified Preparation of the Recombinant Fragment of Triticain-Alpha from *E. coli*

The target 6HIS-Triticain-α-GM (SEQ ID NO:2) and Triticain-α-GM-6HIS (SEQ ID NO:3) proteins are purified by affinity (metal-chelate) chromatography. The preparation of recombinant 6HIS-Triticain-α-GM and Triticain-α-GM-6HIS from cells of the producer strains Rosetta gami B (DE3)/pET15-6HIS-Triticain-α-GM and Rosetta gami B (DE3)/pET15-Triticain-α-GM-6HIS, respectively, includes several stages. The cell culture biomass of the expression culture precipitated by centrifugation is resuspended in 0.02 M phosphate buffer, pH 8.0, containing 0.5 M NaCl and 0.01 M imidazole (buffer A), and homogenized in an ultrasonic disintegrator for 1 min (12×5 s) at 4° C. The supernatant obtained after centrifugation of the lysate (10000×g, 4° C., 15 min) is applied onto a column with nickel-activated iminodiacetate-sepharose equilibrated with buffer A. The chromatography process is carried out on a BioLogic system (BioRad) with detection at 280 nm. The sorbent is washed sequentially with equilibration buffer A. The protein bound to the sorbent is eluted with buffer A containing 0.3 M imidazole. The solution is dialyzed against 0.02 M phosphate buffer, pH 8.0 at 4° C. for 24 h, changing the buffer three times with a fresh one. The concentration of the target protein is estimated using BCA (bicinchoninic acid), aliquoted into glass vials, frozen and lyophilized.

The yield of the recombinant variants of truncated triticain-alpha obtained in this way in soluble form is at least 15 mg (15-24 mg) from 1 L for the bacterial culture Rosetta gami B (DE3)/pET15-6HIS-Triticain-α-GM and at least 5 mg from 1 L for Rosetta gami B (DE3)/pET15-Triticain-α-GM-6HIS. The purity of the obtained preparations according to electrophoretic analysis is at least 85% (FIGS. 1 and 2; it should be noted that the target proteins 6HIS-Triticain-α-GM (SEQ ID NO:2) and Triticain-α-GM-6HIS (SEQ ID NO:3), exhibiting proteolytic activity, undergo autoproteolysis during isolation).

EXAMPLE 5

Expression of the Wheat Triticain-Alpha Fragment in Soluble Form in *P. pastoris*

The histidine-auxotrophic strain *Pichia pastoris* GS115 ($His^-$, $Mut^+$) is used to transform *Pichia pastoris* cells with the yeast expression plasmid pPIC9-Triticain-α-GM. The plasmid pPIC9-Triticain-α-GM is linearized at the BglII site. *Pichia pastoris* cells are transformed by electroporation. Cells of the strain GS115 are plated onto a plate with agarized YPD medium (1% yeast extract, 2% peptone, 2% glucose) and incubated at 30° C. for 2 days until separate colonies appear. 5 ml of YPD medium in a 50 ml flask is inoculated with one colony, and cells are grown overnight at 30° C. in a shaker incubator at 300 rpm. Then, 200 mL of fresh YPD medium are inoculated with 0.2 ml of the overnight culture, and cells are again grown overnight at 30° C. in a shaker incubator until the optical density $A_{600}$ of the cell suspension 1.5 is reached. Cells are precipitated by centrifugation (1500×g, 5 min, 4° C.), the precipitate is washed twice with 200 mL and 100 mL of ice-cold sterile water, respectively, after which the cells are precipitated again and resuspended in 8 ml of cold 1 M sorbitol. Then the cells are precipitated again and resuspended in 0.6 mL of ice-cold 1 M sorbitol. 40 μl of the cell suspension is mixed with 5 μg of the linearized plasmid in 10 μl of TE buffer (0.01 M Tris-HCl, 0.001 M EDTA, pH 8.0). The mixture is placed into a cooled 2 mm cuvette and cooled on ice for 5 min. Then the cuvette is placed into the compartment of the shock chamber of the electroporator and a single pulse is generated. The cuvette is removed from the chamber and 1 ml of ice-cold 1 M sorbitol is quickly added. The contents of the cuvette are transferred to sterile microtubes. 100, 300 and 600 μl of the cell suspension transformed with the linearized plasmid pPIC9-Triticain-α-GM are spread on a Petri dish with minimal histidine-free agarized medium. To survival control, 10 μl of the cell suspensions after electroporation are suspended in 100 μl of 1 M sorbitol and 10 μl are spread on Petri dishes with agarized YPD medium. The dishes are incubated at 30° C. until colonies appear (2-4 days).

Depending on the recombination method and the insertion locus of the linearized plasmid, transformed *Pichia pastoris* GS115 ($Mut^+$) cells may acquire the $Mut^S$ phenotype. To confirm the $Mut^+$ and $Mut^S$ phenotypes of transformants, colonies are plated on plates with minimal agarized medium containing methanol and glucose (MM and MD, respectively), implying that the yeast cells of the $Mut^S$ phenotype divide more slowly in MM medium than in MD medium (as visually assessed by size comparison of the colonies on the MM and MD plates after 2-3 days of incubation at 30° C.). The exact yeast transformants belonging to the $Mut^+$ or $Mut^S$ phenotype is confirmed by polymerase chain reaction. For this, DNA is isolated from the selected clones with MM and MD plates and analyzed by the PCR method using the direct 5AOX1 (gactggttccaattgacaagc) and reverse CACI (gcaaatggcattctgacatcc) primers under amplification conditions: 95° C. for 3 min, denaturation at 95° C. for 30 s, 30 cycles, annealing at 54° C. for 30 s, elongation at 72° C. for 2 min, then 5 min at 72° C. The samples are analyzed by horizontal electrophoresis in a 1% agarose gel stained with ethidium bromide. The size of the amplicons of the DNA of the $Mut^+$ and $Mut^S$ phenotype clones (2140 bp and 1476 bp, respectively) reveals the predominant phenotype ($Mut^+$). The obtained transformants of *Pichia pastoris* GS115/pPIC9-Triticain-α-GM contain at least one copy of a fragment of the triticain-alpha gene. According to the results of analysis, several clones of $Mut^+$ and $Mut^S$ phenotypes are selected for expression of the target recombinant protein.

To obtain double transformants, the plasmid pPIC9K-Triticain-α-GM linearized by the restriction site SalI is transformed into previously obtained *Pichia pastoris* GS115/pPIC9-Triticain-α-GM cells ($Mut^+$ and $Mut^S$). The double transformants were selected on a geneticin-containing medium (0.15 mg/mL).

To study the ability of the *P. pastoris* transformants of the $Mut^+$ and $Mut^S$ phenotypes to secrete y-Triticain-α-GM (SEQ ID NO:4), 4 mL of BMGY medium (1% yeast extract, 2% peptone, 1.34% YNB, $4 \cdot 10^{-5}$% biotin, 1% glycerol, 0.1 M potassium phosphate, pH 6.0) are inoculated with one colony of each transformant clone and control strains from fresh plates. Cell mass is increased at 30° C. in a shaker incubator at 300 rpm until A600 reaches 1 o.u. (for $Mut^+$) or $A_{600}$ 5 o.u. (for $Mut^S$). For AOX-controlled expression induction, cell suspensions in a volume containing 5 o.u. ($Mut^+$) or 25 o.u. ($Mut^S$) are precipitated by centrifugation and the precipitates are resuspended in 5 mL of BMMY medium (1% yeast extract, 2% peptone, 1.34% YNB, $4 \cdot 10^{-5}$% biotin, 0.5% methanol, 0.1 M potassium phosphate, pH 6.0). Cells are incubated for 96 h at 30° C. and 300 rpm. Methanol is added every 24 h to a final concentration of 0.7%. After incubation, the cells are precipitated by centrifugation (4,000×g, 5 min, 4° C.). The supernatants are collected, frozen in liquid nitrogen and stored at −70° C. until further analysis. The presence of recombinant y-Triticain-α-GM in the *P. pastoris* cell culture supernatants is verified by electrophoresis on a 14% polyacrylamide gel with sodium dodecyl sulfate.

EXAMPLE 6

Production Highly Purified Recombinant y-Triticain-α-GM from *Pichia pastoris*

The *Pichia pastoris* GS115/pPIC9-Triticain-α-GM culture supernatant is filtered (0.45 μm) and dialyzed against a 0.02 M sodium phosphate solution, pH 8.0, at 4° C. for 24 h, replacing the buffer with fresh three times. The dialysate is concentrated by ultrafiltration on an Amicon cell with an RC-10 membrane (Millipore) and applied to a column with a Sephacryl S-200HR sorbent equilibrated in 0.02 M phosphate buffer, pH 8.0, containing 130 mM NaCl. The gel filtration process is carried out at a rate of 0.5 mL/min, 6 mL fractions are collected and analyzed for the target protein by electrophoretic analysis and proteolytic activity evaluation. The purified protein is concentrated on an Amicon cell with an RC-10 membrane (Millipore), the concentration is analyzed using BCA (bicinchoninic acid), aliquoted into glass vials, frozen and lyophilized.

Figure 3:
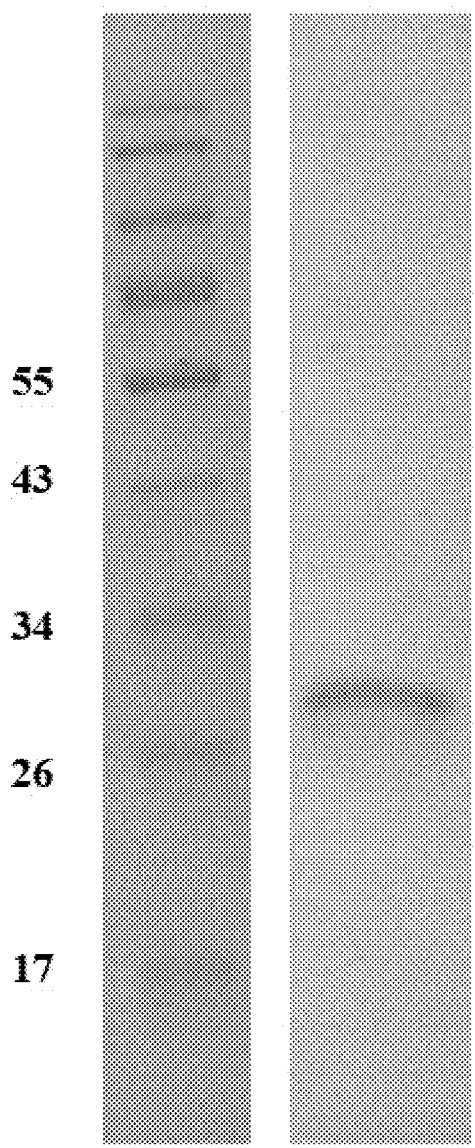
FIG. 3 shows the recombinant truncated triticain-alpha (SEQ ID NO:4, y-Triticain-α-GM, expressed in *P. pastoris* cells) after chromatographic isolation in a 14% polyacrylamide gel in the presence of SDS (M are protein markers of molecular weight, kDa).

The yield of recombinant y-Triticain-α-GM obtained in this way (SEQ ID NO:4) is 80-300 mg per liter of the yeast culture (with a purity of at least 90% according to electrophoretic analysis, FIG. 3; it should be noted that the target protein y-Triticain-α-GM (SEQ ID NO: 4) undergoes autoproteolysis during secretion).

EXAMPLE 7

Evaluation of the Proteolytic Activity of Variants of Recombinant Proteins of Truncated Triticain-Alpha (6HIS-Triticain-α-GM, Triticain-α-GM-6HIS, and y-Triticain-α-GM)

The enzymatic (proteolytic) activity of recombinant truncated triticain-alpha is evaluated by its ability to hydrolyze the synthetic model peptide substrate PLVQ-AMK conjugated with 7-amino-4-methylcoumarin (AMC), with the analysis of hydrolysis products by the fluorescence intensity of free AMC. The sequence and structure of the selected PLVQ (proline-leucine-valine-glutamine) peptide, which is a gluten fragment, are optimal for the binding and hydrolysis by triticain-alpha [application W02008115428 A2, Sep. 25, 2008].

Figure 4:
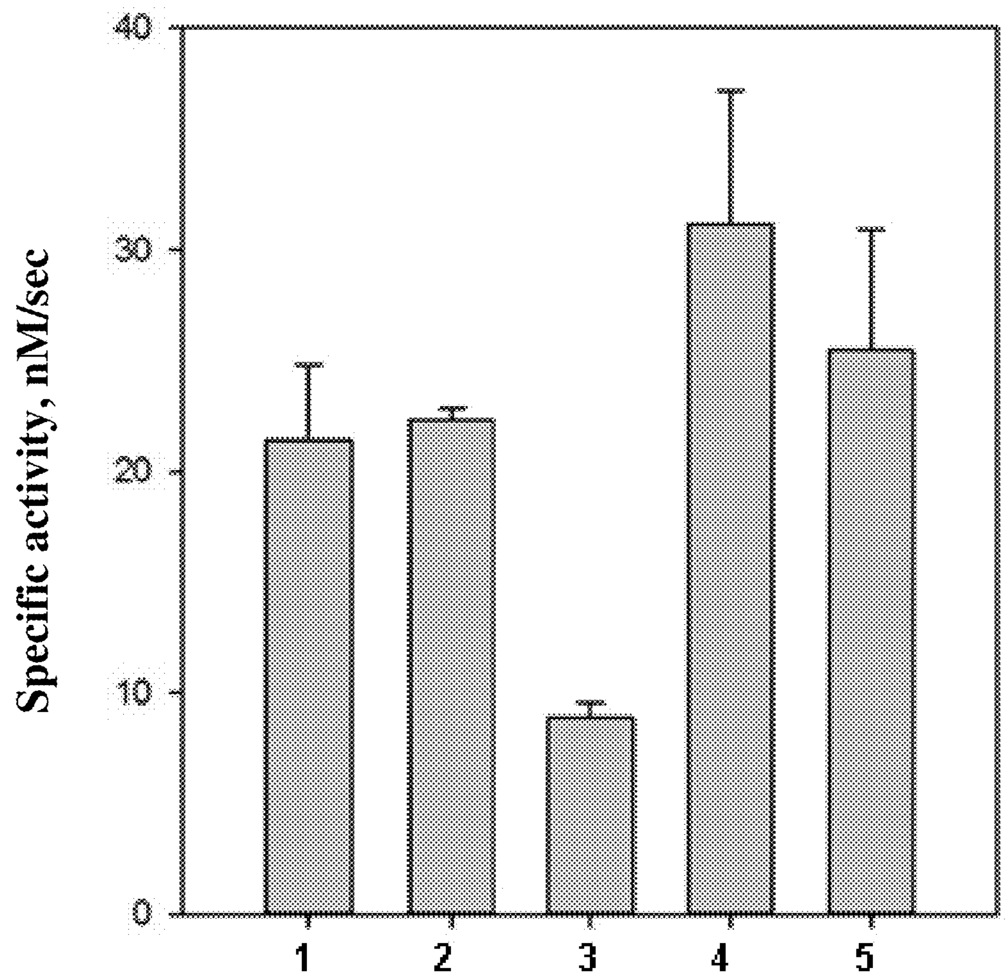
FIG. 4 shows a histogram showing the specific (proteolytic) activity of variants of recombinant proteins of truncated triticain-alpha and papain (as a control for cysteine papain-like protease): 1—papain; 2—the recombinant fragment of triticain-alpha from the insoluble fraction; 3—truncated triticain-alpha expressed in *P. pastoris* cells (SEQ ID NO:4, y-Triticain-α-GM); 4—truncated triticain-alpha with an N-terminal polyhistidine sequence (SEQ ID NO:2, 6HIS-Triticain-α-GM); 5—the truncated triticain-alpha with a C-terminal polyhistidine sequence (SEQ ID NO:3, Triticain-α-GM-6HIS).

Analysis is carried out at 25° C. in a reaction mixture consisting of 20 nM of the target protein (recombinant triticain-alpha) and 50 μM PLVQ-AMC in 200 mM acetate buffer, pH 5.6, containing 100 mM NaCl, 15 mM 2-mercaptoethanol, 0.6 mM EDTA, and 0.5% DMSO. The amount of the PLVQ-AMC hydrolyzed substrate is estimated by the fluorescence intensity of free AMC using a multimode automatic spectrofluorimeter with a fluorescence excitation wavelength of 360 nm and a fluorescence emission wavelength of 460 nm. The reaction rate is determined by the plot of the dependence of the substrate amount (mol) on the hydrolysis time (s), followed by processing of the obtained data using linear regression. For representativeness, data on specific activity are presented as a histogram (FIG. 4).

The activity of the truncated triticain-alpha preparations obtained in soluble form was compared with activities of the truncated triticain-alpha preparations obtained previously in an insoluble form and papain.

The activity of the truncated triticain-alpha protein preparations obtained in the soluble form, 6HIS-Triticain-α-GM (SEQ ID NO:2) and Triticain-α-GM-6HIS (SEQ ID NO:3), significantly exceeded the activity of the truncated triticain-alpha preparation 6HIS-Triticain-α-GM, obtained in an insoluble form, as well as that of papain, which is a significant advantage of the preparations we obtained in the framework of this application. The activity of the truncated triticain-alpha y-Triticain-α-GM preparation (SEQ ID NO:4) obtained in the yeast expression system was lower than the activity of the truncated triticain-alpha 6HIS-Triticain-α-GM preparation obtained in an insoluble form, and that of papain; however, taking into account the high content of y-Triticain-α-GM protein in the preparation and its high yield upon expression, this result is also industrially applicable and technically significant.

The advantages of the claimed technical solution are, firstly, the preparation of a proteolytically active preparation of triticain-alpha, consisting of a propeptide domain (prodomain) and a catalytic domain of full-sized wheat triticain-alpha, which can be used to design novel, more effective medicinal enzymatic agents, as well as for research purposes, in particular, to study the functioning of papain-like cysteine protease; secondly, the possibility of obtaining variants of proteolytically active triticain-alpha in soluble form in both bacterial and yeast cells; and thirdly, a simplified method for isolating recombinant protein variants from *E. coli* by eliminating the in vitro refolding stage, i.e. a time-consuming and difficult to validate procedure, which subsequently will serve as the basis for the design of enzymatic preparations to treat certain diseases (in particular, celiac disease).

The invention claimed is:

1. A biologically active protein preparation with the specific activity of papain-like cysteine protease, wherein the protein is expressed in soluble form and comprises the amino acid sequence encoded by SEQ ID NO: 2, 3 or 4.

* * * * *

```
SEQUENCE LISTING

<160> NUMBER OF SEQ ID NOS: 13

<210> SEQ ID NO 1
```

<211> LENGTH: 1419
<212> TYPE: DNA
<213> ORGANISM: Triticum aestivum

<400> SEQUENCE: 1

```
catatgcatc atcatcatca tcatgccatg aggagctcca tggccctctt ggcggcggcg      60

ctgctgctgc tggtgtcgct ggcggcggcg gcggacatgt cgatcgtgtc gtacggggag     120

cggagcgagg aggaggtgcg gcggatgtac gccgagtgga tgtccgagca ccgcaggacg     180

tacaacgcca tcggcgagga ggagcgccgc ttcgaggtct tcagggacaa cctccgctac     240

atcgaccagc acaacgccgc cgccgacgcc gggctccact ccttccgcct cggcctcaac     300

cgcttcgccg acctcaccaa cgaggagtac cgcagcacgt acctgggcgc ccggaccaag     360

ccggaccggg agcggaagct cagcgccagg taccaggccg acgacaacga ggagctgccg     420

gagaccgtcg actggaggaa gaagggggcc gttgctgcca tcaaggacca gggcggctgc     480

gggagctgct gggctttctc agcaatagca gctgttgaag gcatcaacca gattgttacg     540

ggcgacatga tccctctgtc cgagcaagag cttgttgact gtgacacttc atacaacgag     600

ggatgcaatg gaggtctgat ggactatgcg tttgagttca tcattaacaa tggcggtatc     660

gactctgagg aggactaccc ctacaaggag agggacaacc gttgcgatgc taacaagaaa     720

aatgcgaagg ttgttaccat tgatgggtac gaggatgtgc ccgtgaacag tgagaagagt     780

ctgcagaagg cagttgcaaa ccagcccatc agtgttgcga ttgaggctgg tggcagggca     840

ttccagctct acaaatcggg tatcttcact ggaacctgtg gaacagcact tgaccatggt     900

gtcgccgccg ttggttatgg tacagagaac ggcaaggact actggctcgt caggaactcc     960

tggggtaccg tctggggaga ggatggttac atccggatgg agcgtaacat caaggcatcc    1020

agtggcaaat gtggtattgc cgttgagcct tcctacccga cgaagacggg cgagaacccc    1080

cctaaccccg gcccaactcc accatctccc gccccaccgt cttccgtctg tgacagctac    1140

aacgagtgcc ccgcgagcac gacctgctgc tgcatctacg agtacggcaa ggagtgcttc    1200

gcctggggct gttgcccact cgagggtgct acctgctgcg atgatcacta cagctgctgc    1260

cctcataact atcccatctg caacacccag cagggaacct gccttgcggc caaggacagt    1320

ccactgtcag tgaaggctca gaggcgtacc ctggccaagc ctatcggtgc tttctctgtc    1380

attgcaactg acggcaagaa aagtagcgcg taaggatcc                           1419
```

<210> SEQ ID NO 2
<211> LENGTH: 1047
<212> TYPE: DNA
<213> ORGANISM: Triticum aestivum

<400> SEQUENCE: 2

```
catatgggca gcagccatca tcatcatcat cacagcagcg gcctggtgcc gcgcggcagc      60

catatgtcga tcgtgtcgta cggggagcgg agcgaggagg aggtgcggcg gatgtacgcc     120

gagtggatgt ccgagcaccg caggacgtac aacgccatcg gcgaggagga gcgccgcttc     180

gaggtcttca gggacaacct ccgctacatc gaccagcaca acgccgccgc cgacgccggg     240

ctccactcct tccgcctcgg cctcaaccgc ttcgccgacc tcaccaacga ggagtaccgc     300

agcacgtacc tgggcgcccg gaccaagccg gaccgggagc ggaagctcag cgccaggtac     360

caggccgacg acaacgagga gctgccggag accgtcgact ggaggaagaa gggggccgtt     420

gctgccatca aggaccaggg cggctgcggg agctgctggg ctttctcagc aatagcagct     480

gttgaaggca tcaaccagat tgttacgggc gacatgatcc ctctgtccga gcaagagctt     540
```

```
gttgactgtg acacttcata caacgaggga tgcaatggag gtctgatgga ctatgcgttt    600

gagttcatca ttaacaatgg cggtatcgac tctgaggagg actacccccta caaggagagg    660

gacaaccgtt gcgatgctaa caagaaaaat gcgaaggttg ttaccattga tgggtacgag    720

gatgtgcccg tgaacagtga gaagagtctg cagaaggcag ttgcaaacca gcccatcagt    780

gttgcgattg aggctggtgg cagggcattc cagctctaca aatcgggtat cttcactgga    840

acctgtggaa cagcacttga ccatggtgtc gccgccgttg gttatggtac agagaacggc    900

aaggactact ggctcgtcag gaactcctgg ggtaccgtct ggggagagga tggttacatc    960

cggatggagc gtaacatcaa ggcatccagt ggcaaatgtg gtattgccgt tgagccttcc   1020

tacccgacga agacgggcta actcgag                                        1047
```

<210> SEQ ID NO 3
<211> LENGTH: 1017
<212> TYPE: DNA
<213> ORGANISM: Triticum aestivum

<400> SEQUENCE: 3

```
atggcggaca tgtcgatcgt gtcgtacggg gagcggagcg aggaggaggt gcggcggatg     60

tacgccgagt ggatgtccga gcaccgcagg acgtacaacg ccatcggcga ggaggagcgc    120

cgcttcgagg tcttcaggga caacctccgc tacatcgacc agcacaacgc cgccgccgac    180

gccgggctcc actccttccg cctcggcctc aaccgcttcg ccgacctcac caacgaggag    240

taccgcagca cgtacctggg cgcccggacc aagccggacc gggagcggaa gctcagcgcc    300

aggtaccagg ccgacgacaa cgaggagctg ccggagaccg tcgactggag gaagaagggg    360

gccgttgctg ccatcaagga ccagggcggc tgcgggagct gctgggcttt ctcagcaata    420

gcagctgttg aaggcatcaa ccagattgtt acgggcgaca tgatccctct gtccgagcaa    480

gagcttgttg actgtgacac ttcatacaac gagggatgca atggaggtct gatggactat    540

gcgtttgagt tcatcattaa caatggcggt atcgactctg aggaggacta cccctacaag    600

gagagggaca accgttgcga tgctaacaag aaaaatgcga aggttgttac cattgatggg    660

tacgaggatg tgcccgtgaa cagtgagaag agtctgcaga aggcagttgc aaaccagccc    720

atcagtgttg cgattgaggc tggtggcagg gcattccagc tctacaaatc gggtatcttc    780

actggaacct gtggaacagc acttgaccat ggtgtcgccg ccgttggtta tggtacagag    840

aacggcaagg actactggct cgtcaggaac tcctggggta ccgtctgggg agaggatggt    900

tacatccgga tggagcgtaa catcaaggca tccagtggca aatgtggtat tgccgttgag    960

ccttcctacc cgacgaagac gggcctcgag caccaccacc accaccactg actcgag      1017
```

<210> SEQ ID NO 4
<211> LENGTH: 1262
<212> TYPE: DNA
<213> ORGANISM: Triticum aestivum

<400> SEQUENCE: 4

```
atgagatttc cttcaatttt tactgcagtt ttattcgcag catcctccgc attagctgct     60

ccagtcaaca ctacaacaga agatgaaacg gcacaaattc cggctgaagc tgtcatcggt    120

tactcagatt tagaagggga tttcgatgtt gctgttttgc cattttccaa cagcacaaat    180

aacgggttat tgtttataaa tactactatt gccagcattg ctgctaaaga agaaggggta    240

tctctcgaga aaagagaggc tgaagcttac gtagaattct ccatcgtgtc gtacggggag    300
```

-continued

```
cggagcgagg aggaggtgcg gcggatgtac gccgagtgga tgtccgagca ccgcaggacg    360

tacaacgcca tcggcgagga ggagcgccgc ttcgaggtct tcagggacaa cctccgctac    420

atcgaccagc acaacgccgc cgccgacgcc gggctccact ccttccgcct cggcctcaac    480

cgcttcgccg acctcaccaa cgaggagtac cgcagcacgt acctgggcgc ccggaccaag    540

ccggaccggg agcggaagct cagcgccagg taccaggccg acgacaacga ggagctgccg    600

gagaccgtcg actggaggaa gaagggggcc gttgctgcca tcaaggacca gggcggctgc    660

gggagctgct gggctttctc agcaatagca gctgttgaag gcatcaacca gattgttacg    720

ggcgacatga tccctctgtc cgagcaagag cttgttgact gtgacacttc atacaacgag    780

ggatgcaatg gaggtctgat ggactatgcg tttgagttca tcattaacaa tggcggtatc    840

gactctgagg aggactaccc ctacaaggag agggacaacc gttgcgatgc taacaagaaa    900

aatgcgaagg ttgttaccat tgatgggtac gaggatgtgc ccgtgaacag tgagaagagt    960

ctgcagaagg cagttgcaaa ccagcccatc agtgttgcga ttgaggctgg tggcagggca   1020

ttccagctct acaaatcggg tatcttcact ggaacctgtg gaacagcact tgaccatggt   1080

gtcgccgccg ttggttatgg tacagagaac ggcaaggact actggctcgt caggaactcc   1140

tggggtaccg tctggggaga ggatggttac atccggatgg agcgtaacat caaggcatcc   1200

agtggcaaat gtggtattgc cgttgagcct tcctacccga cgaagacggg ctaagcggcc   1260

gc                                                                  1262
```

```
<210> SEQ ID NO 5
<211> LENGTH: 27
<212> TYPE: DNA
<213> ORGANISM: Artificial Sequence
<220> FEATURE:
<223> OTHER INFORMATION: synthesized

<400> SEQUENCE: 5

gctgctgctg ctgctgctgc tgctgct                                         27


<210> SEQ ID NO 6
<211> LENGTH: 51
<212> TYPE: DNA
<213> ORGANISM: Artificial Sequence
<220> FEATURE:
<223> OTHER INFORMATION: synthesized

<400> SEQUENCE: 6

ccccatatgc atcatcatca tcatcatgcc atgaggagct ccatggccct c              51


<210> SEQ ID NO 7
<211> LENGTH: 31
<212> TYPE: DNA
<213> ORGANISM: Artificial Sequence
<220> FEATURE:
<223> OTHER INFORMATION: synthesized

<400> SEQUENCE: 7

gggggatcct tacgcgctac ttttcttgcc g                                    31


<210> SEQ ID NO 8
<211> LENGTH: 27
<212> TYPE: DNA
<213> ORGANISM: Artificial Sequence
<220> FEATURE:
<223> OTHER INFORMATION: synthesized

<400> SEQUENCE: 8
```

```
tatacatatg tcgatcgtgt cgtacgg                                          27


<210> SEQ ID NO 9
<211> LENGTH: 26
<212> TYPE: DNA
<213> ORGANISM: Artificial Sequence
<220> FEATURE:
<223> OTHER INFORMATION: synthesized

<400> SEQUENCE: 9

ttctcgagtt agcccgtctt cgtcgg                                           26


<210> SEQ ID NO 10
<211> LENGTH: 27
<212> TYPE: DNA
<213> ORGANISM: Artificial Sequence
<220> FEATURE:
<223> OTHER INFORMATION: synthesized

<400> SEQUENCE: 10

ataccatggc gctgccggag accgtcg                                          27


<210> SEQ ID NO 11
<211> LENGTH: 47
<212> TYPE: DNA
<213> ORGANISM: Artificial Sequence
<220> FEATURE:
<223> OTHER INFORMATION: synthesized

<400> SEQUENCE: 11

attctcgagt cagtggtggt ggtggtggtg gcccgtcttc gtcgggt                    47


<210> SEQ ID NO 12
<211> LENGTH: 25
<212> TYPE: DNA
<213> ORGANISM: Artificial Sequence
<220> FEATURE:
<223> OTHER INFORMATION: synthesized

<400> SEQUENCE: 12

tgaattctcc atcgtgtcgt acggg                                            25


<210> SEQ ID NO 13
<211> LENGTH: 29
<212> TYPE: DNA
<213> ORGANISM: Artificial Sequence
<220> FEATURE:
<223> OTHER INFORMATION: synthesized

<400> SEQUENCE: 13

attgcggccg cttagcccgt cttcgtcgg                                        29
```